(12) United States Patent
Liu et al.

(10) Patent No.: US 8,891,733 B2
(45) Date of Patent: *Nov. 18, 2014

(54) POWER AND COMMUNICATION INTERFACE BETWEEN A DIGITAL X-RAY DETECTOR AND AN X-RAY IMAGING SYSTEM

(75) Inventors: James Zhengshe Liu, Salt Lake City, UT (US); Scott William Petrick, Sussex, WI (US); Luke Gerard Beno, Green Bay, WI (US)

(73) Assignee: General Electric Company, Schenectady, NY (US)

( * ) Notice: Subject to any disclaimer, the term of this patent is extended or adjusted under 35 U.S.C. 154(b) by 329 days.

This patent is subject to a terminal disclaimer.

(21) Appl. No.: 13/469,592

(22) Filed: May 11, 2012

(65) Prior Publication Data

US 2013/0301803 A1 Nov. 14, 2013

(51) Int. Cl.
*H05G 1/08* (2006.01)

(52) U.S. Cl.
USPC ............................................. 378/91; 378/98.8

(58) Field of Classification Search
CPC ...... A61B 6/563; A61B 6/4405; A61B 6/467; A61B 6/4233; H05G 1/10; H05G 1/56; H05G 1/32
USPC .................... 378/91, 98.8, 101, 102, 114–116
See application file for complete search history.

(56) References Cited

U.S. PATENT DOCUMENTS

| | | | |
|---|---|---|---|
| 3,705,984 A | 12/1972 | Westenberger | |
| 4,414,683 A | 11/1983 | Robinson | |
| 5,022,065 A | 6/1991 | Wijkstrom | |
| 5,226,068 A | 7/1993 | Strawder | |
| 5,473,664 A | 12/1995 | Strawder | |
| 5,479,471 A | 12/1995 | Buckland | |
| 5,563,926 A | 10/1996 | Brotzman | |
| 5,640,439 A | 6/1997 | Strawder | |
| 5,673,302 A | 9/1997 | Kriecha et al. | |
| 5,708,840 A | 1/1998 | Kikinis et al. | |
| 5,729,587 A | 3/1998 | Betz | |
| 5,844,961 A | 12/1998 | McEvoy et al. | |
| 5,867,553 A | 2/1999 | Gordon et al. | |
| 5,877,501 A | 3/1999 | Ivan et al. | |
| 6,017,149 A | 1/2000 | Strawder | |
| 6,044,131 A | 3/2000 | McEvoy et al. | |
| 6,143,970 A | 11/2000 | Kowzan | |
| 6,337,712 B1 | 1/2002 | Shiota et al. | |
| 6,440,072 B1 | 8/2002 | Schuman et al. | |
| 6,475,146 B1 | 11/2002 | Frelburger et al. | |
| 6,833,867 B1 | 12/2004 | Anderson | |
| 7,022,075 B2 | 4/2006 | Grunwald et al. | |

(Continued)

*Primary Examiner* — Courtney Thomas
(74) *Attorney, Agent, or Firm* — Patrick Kim

(57) ABSTRACT

A system for eliminating image artifacts caused by electromagnetic interference (EMI) on a portable digital x-ray detector that is capable of non-contact wireless inductively coupled power transfer. An X-ray imaging system comprising a portable digital X-ray detector having detector circuitry coupled to at least one receiver coil, and a power source including a power supply coupled to a signal filter device and coupled to at least one transmitter coil, wherein the power source is coupled to a detector receptacle of the X-ray imaging system, and wherein the at least one receiver coil and the at least one transmitter coil are inductively coupled to each other when the portable digital X-ray detector is located within the detector receptacle of the X-ray imaging system to transfer power from the power supply to the detector circuitry.

29 Claims, 11 Drawing Sheets

(56) References Cited

U.S. PATENT DOCUMENTS

| | | |
|---|---|---|
| 7,261,465 B2 | 8/2007 | Butzine et al. |
| 7,270,477 B1 | 9/2007 | Kari |
| 7,342,998 B2 | 3/2008 | Kump et al. |
| 7,696,722 B2 | 4/2010 | Utschig et al. |
| 7,715,187 B2 | 5/2010 | Hotelling et al. |
| 7,997,798 B2 | 8/2011 | Liu et al. |
| 2003/0078072 A1 | 4/2003 | Serceki et al. |
| 2005/0135564 A1 | 6/2005 | Dippl et al. |
| 2005/0136892 A1 | 6/2005 | Osterling et al. |
| 2005/0197093 A1 | 9/2005 | Wiklof et al. |
| 2006/0061323 A1 | 3/2006 | Cheng et al. |
| 2006/0067474 A1 | 3/2006 | Schmitt |
| 2006/0070384 A1 | 4/2006 | Ertel |
| 2006/0108977 A1 | 5/2006 | Kagermeier et al. |
| 2006/0213845 A1 | 9/2006 | Utshig |
| 2007/0004980 A1 | 1/2007 | Warner et al. |
| 2007/0140424 A1 | 6/2007 | Serecki |
| 2007/0180046 A1 | 8/2007 | Cheung et al. |
| 2007/0269010 A1 | 11/2007 | Turner |
| 2008/0144777 A1 | 6/2008 | Wilson |
| 2008/0263905 A1 | 10/2008 | Tai |
| 2010/0019720 A1 | 1/2010 | Liu et al. |
| 2013/0301801 A1* | 11/2013 | Liu et al. .......... 378/91 |

* cited by examiner

POWER AND COMMUNICATION INTERFACE BETWEEN A DIGITAL X-RAY DETECTOR AND AN X-RAY IMAGING SYSTEM

BACKGROUND OF THE INVENTION

This disclosure relates generally to X-ray imaging systems, and more particularly to techniques for power and communication coupling between a portable wireless X-ray detector and an X-ray imaging system.

A number of X-ray imaging systems of various designs are known and are presently in use. Such systems generally are based upon generation of X-rays that are directed toward a subject of interest. The X-rays traverse the subject and impact a film or a digital X-ray detector. Increasingly, such X-ray imaging systems use digital circuitry for detecting the X-rays, which are attenuated, scattered or absorbed by the intervening structures of the subject. In medical imaging contexts, for example, such systems may be used to visualize the internal structures, tissues and organs of a subject for the purpose of screening and/or diagnosing ailments, illnesses or diseases. In other contexts, parts, structures, baggage, parcels and other subjects may be imaged to assess their contents, structural integrity or other purposes.

In existing X-ray imaging systems, power and communication is provided by the X-ray imaging system to the portable digital X-ray detector through connectors, cabling and/or wiring. The portable digital X-ray detector typically includes a connector that is directly coupled to a connector in a detector receptacle that is directly coupled to a power source and/or communication circuitry of the X-ray imaging system. The robustness of the wiring, cabling and connectors has always been an issue due to wear and tear on the wiring and cabling, and contamination of connector contacts. In addition, the wiring and cabling is cumbersome and prone to maintenance problems. Therefore, the interconnection between the X-ray imaging system and the portable digital X-ray detector has not been reliable. The present disclosure eliminates the connectors, cabling and wiring between the X-ray imaging system and the portable digital X-ray detector by incorporating inductive power coupling and capacitive communication coupling. The present disclosure also minimizes or eliminates any electromagnetic interference (EMI) that may occur from the inductive or capacitive coupling and present itself as image artifacts on X-ray images produced by the X-ray detector.

Therefore, there is a need for an improved, more robust power and communication interface between an X-ray imaging system and a portable digital X-ray detector that improves reliability and eliminates image artifacts caused by EMI.

BRIEF DESCRIPTION OF THE INVENTION

In accordance with an aspect of the present disclosure, an X-ray imaging system comprising a portable digital X-ray detector including detector circuitry coupled to a detector battery and coupled to at least one receiver coil, and a power source including a power supply coupled to an on/off switch and coupled to at least one transmitter coil, wherein the power source is coupled to a detector receptacle of the X-ray imaging system, and wherein the at least one receiver coil and the at least one transmitter coil are inductively coupled to each other when the portable digital X-ray detector is located within the detector receptacle of the X-ray imaging system to transfer power from the power supply to the detector battery when the on/off switch is in an on position.

In accordance with an aspect of the present disclosure, an X-ray imaging system comprising a portable digital X-ray detector including detector circuitry coupled to a detector battery and coupled to at least one receiver coil, and a power source including a power supply coupled to a signal filter device and coupled to at least one transmitter coil, wherein the power source is coupled to a detector receptacle of the X-ray imaging system, and wherein the at least one receiver coil and the at least one transmitter coil are inductively coupled to each other when the portable digital X-ray detector is located within the detector receptacle of the X-ray imaging system to transfer power from the power supply to the detector battery.

In accordance with an aspect of the present disclosure, an X-ray imaging system comprising a portable digital X-ray detector including detector circuitry coupled to at least one receiver coil, and a power source including a power supply coupled to a signal filter device and coupled to at least one transmitter coil, wherein the power source is coupled to a detector receptacle of the X-ray imaging system, and wherein the at least one receiver coil and the at least one transmitter coil are inductively coupled to each other when the portable digital X-ray detector is located within the detector receptacle of the X-ray imaging system to transfer power from the power supply to the detector circuitry.

In accordance with an aspect of the present disclosure, a portable wireless digital X-ray detector comprising detector circuitry coupled to a detector battery and charging circuitry, at least one receiver coil coupled to the charging circuitry, a wireless antenna coupled to the detector circuitry, and EMI shielding protecting the detector circuitry, detector battery and charging circuitry from EMI.

In accordance with an aspect of the present disclosure, a portable wireless digital X-ray detector comprising detector circuitry coupled to at least one receiver coil, a wireless antenna coupled to the detector circuitry, and EMI shielding protecting the detector circuitry from EMI.

Various other features, aspects, and advantages will be made apparent to those skilled in the art from the accompanying drawings and detailed description thereof.

DETAILED DESCRIPTION OF THE INVENTION

Figure 1:
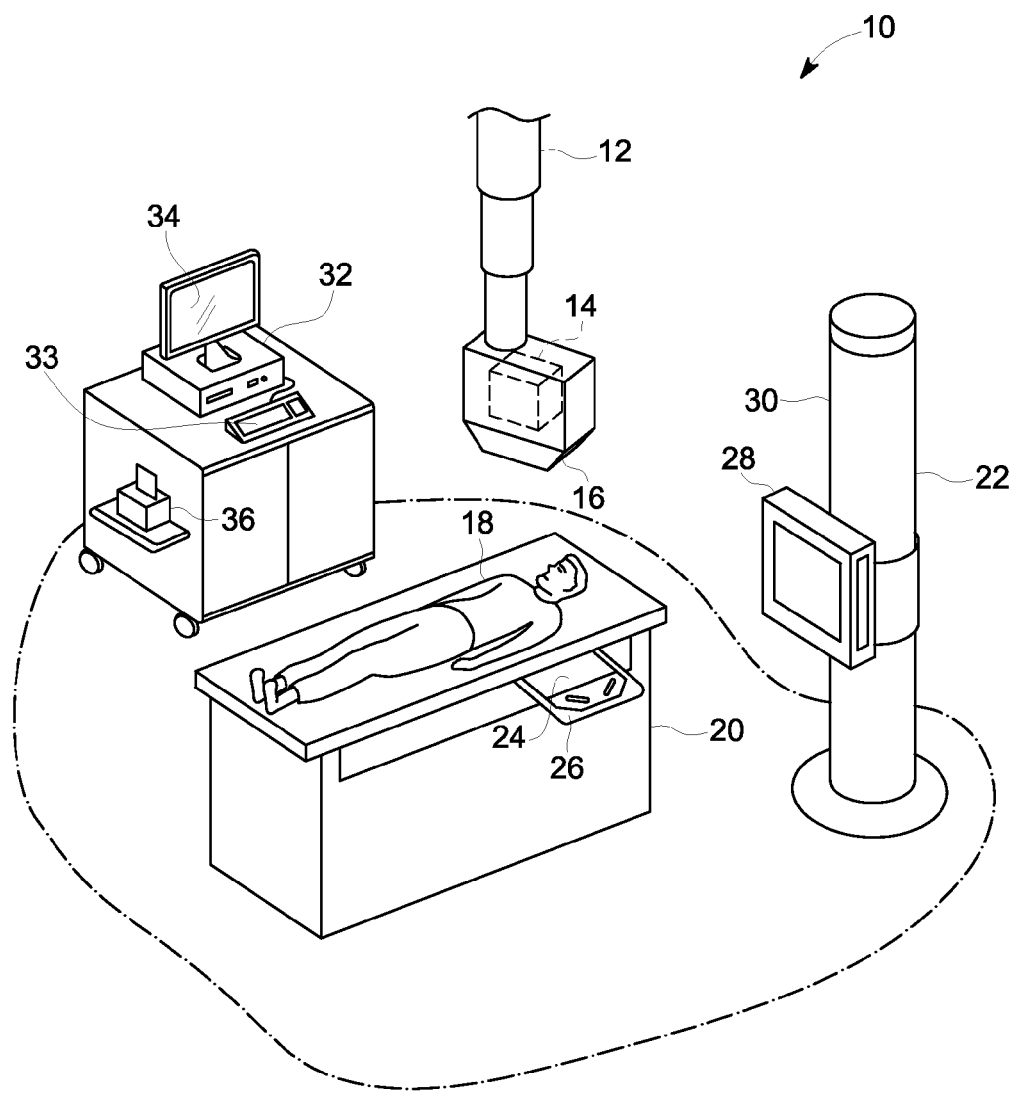
FIG. 1 is a perspective view of an exemplary embodiment of a fixed X-ray imaging system.

Referring to the drawings, FIG. 1 illustrates a perspective view of an exemplary embodiment of a fixed X-ray imaging system 10. In the illustrated embodiment, the fixed X-ray imaging system 10 is a digital X-ray imaging system. The fixed X-ray imaging system 10 is designed both to acquire image data and to process the image data for display. Throughout the following discussion, however, while basic and background information is provided on the digital X-ray imaging system being used in medical applications, it should be understood that the digital X-ray imaging system may be used in different applications (e.g., projection X-ray imaging, computed tomography imaging, tomosynthesis imaging, etc.) and for different purposes (e.g., parcel, baggage, vehicle and part inspection, etc.).

In the embodiment illustrated in FIG. 1, the fixed X-ray imaging system 10 may be a stationary system disposed in a fixed X-ray imaging room. It will be appreciated, however, that the present disclosure may also be employed with other imaging systems, including a mobile X-ray imaging system in other embodiments, such as that generally depicted in and described below with respect to FIG. 2. The fixed X-ray imaging system 10 includes an overhead tube support arm 12 for positioning an X-ray source 14, such as an X-ray tube, and a collimator 16 with respect to a subject 18 being imaged on a table 20 or a wall stand 22, and an X-ray detector 24. The X-ray detector 24 is preferably a digital X-ray detector. The X-ray detector 24 is configured to acquire X-ray image data for a particular type of imaging (e.g., fluoroscopic and radiographic imaging).

The fixed X-ray imaging system 10 is designed to create images of a subject 18 being imaged by means of an X-ray beam emitted by X-ray source 14, and passing through collimator 16, which forms and confines the X-ray beam to a desired region, wherein the subject 18, such as a human patient, an animal or an object, is positioned. A portion of the X-ray beam passes through or around the subject 18, and is altered by attenuation and/or absorption of tissues within the subject 18, and continues on toward and impacts the X-ray detector 24. The X-ray detector 24 converts x-ray photons received on its surface to lower energy light photons, and subsequently to electric signals, which are acquired and processed to reconstruct an image of internal anatomy or structure within the subject 18.

The fixed X-ray imaging system 10 may be used with one or both of a table 20 and a wall stand 22 to facilitate image acquisition. The table 20 and the wall stand 22 may be configured to receive an X-ray detector 24. For example, the table 20 may include a detector receptacle 26 for receiving an X-ray detector 24 therein. The X-ray detector 24 may be placed in the detector receptacle 26 and a subject 18 being imaged may be positioned on the table 20 between the X-ray source 14 and the detector 24 to enable image data to be acquired via the X-ray detector 24 located within the detector receptacle 26. The wall stand 22 preferably includes a vertical support column 30 and a detector receptacle 28 for receiving an X-ray detector 24 therein. The X-ray detector 24 may be placed in the detector receptacle 28 and the detector receptacle 28 containing the detector 24 may be moved vertically up and down along the vertical support column 30, so that a region of interest of a subject 18 being imaged may be positioned adjacent the detector receptacle 28 to enable image data to be acquired via the X-ray detector 24 located within the detector receptacle 28.

Also depicted in FIG. 1, the fixed X-ray imaging system 10 includes a workstation 32. In an exemplary embodiment, the workstation 32 may include a computer, processor, memory, firmware and software to provide functionality of the fixed X-ray imaging system 10 such that a user (not shown), by interacting with the workstation 32 may control operation of the overhead tube support arm 12, X-ray source 14, collimator 16, wall stand 22, X-ray detector 24 and/or perform image processing on acquired image data. The workstation 32 may include a display 34 and a printer 36, and may be coupled to a picture archiving and communications system (PACS). The PACS might be coupled to remote clients, such as a radiology information system (RIS) or a hospital information system (HIS), or to an internal or external network, so that others at different locations may gain access to image data from the X-ray imaging system. The display 34 may be configured to display patient data and reconstructed X-ray images based upon X-ray image data. In an exemplary embodiment, the display 34 may be a touch-screen display. The workstation 32 may also include an input device 33 (e.g., keyboard), wherein the input device 33 or touch-screen display 34 is configured to input data (e.g., patient information), imaging related information (e.g., type of X-ray source, imaging techniques, imaging parameters, etc.) and/or commands (e.g., to the detector) to form a DICOM image header.

Figure 2:
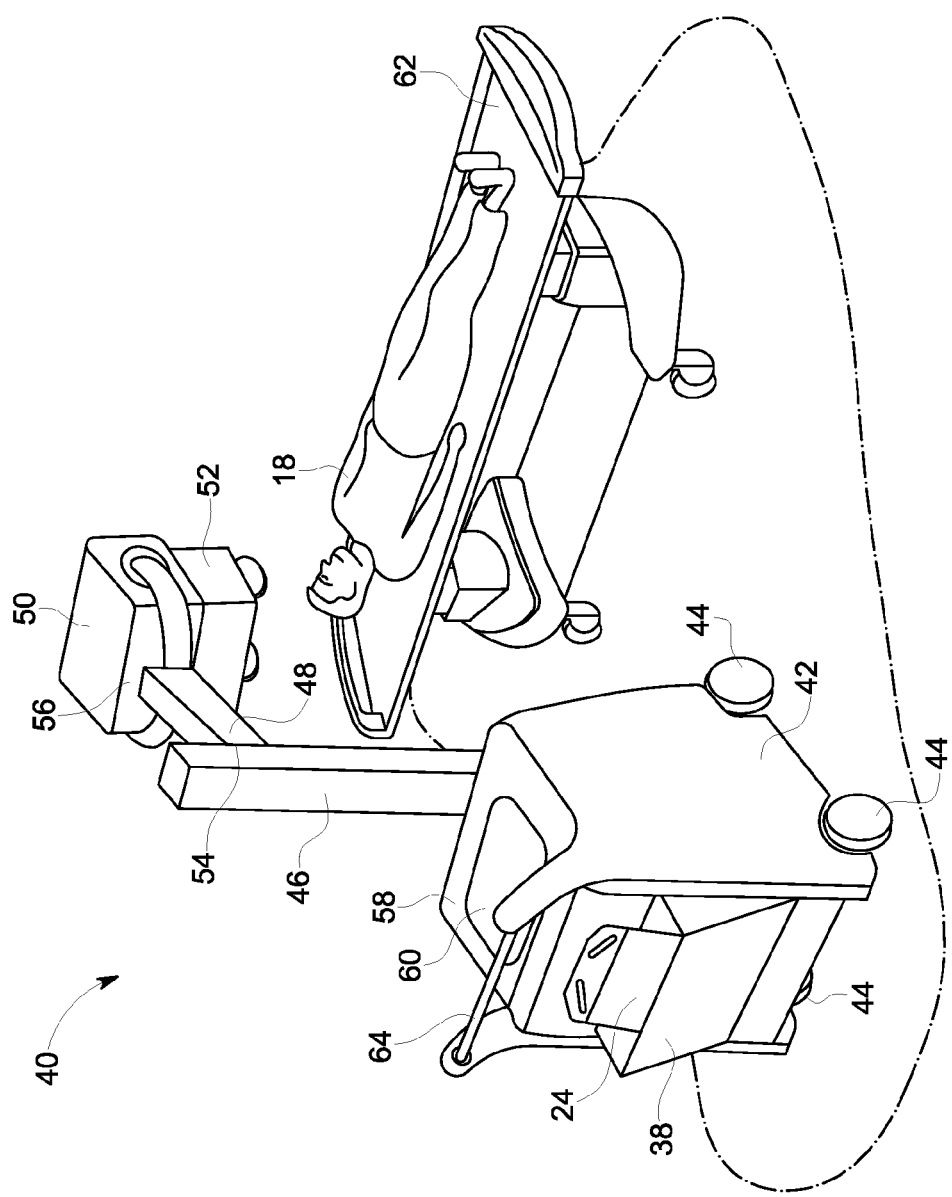
FIG. 2 is a perspective view of an exemplary embodiment of a mobile X-ray imaging system.

FIG. 2 illustrates a perspective view of an exemplary embodiment of a mobile X-ray imaging system 40. The mobile X-ray imaging system 40 may be moved to a patient room, an emergency room, a surgical room, or any other space to enable imaging of a subject 18 without requiring transport of the subject 18 to a dedicated fixed X-ray imaging room. The mobile X-ray imaging system 40 may include a base unit 42 with a plurality of wheels 44 mounted to a bottom of the base unit 42, a vertical support column 46 attached to the base unit 42, a horizontal support arm 48 with a first end 54 coupled to the vertical support column 46, an X-ray source 50 and collimator 52 mounted to a second end 56 of the horizontal support arm 48, and a detector receptacle 38 coupled to the base unit 42 for receiving and storing an X-ray detector 24 therein.

The base unit 42 may include an operator workstation 58 and a display 60 that enables a user to operate the mobile X-ray imaging system 40 and to display images acquired during an imaging procedure of the subject 18. The operator workstation 58 may include a computer, processor, memory, firmware and software to provide functionality of the mobile X-ray imaging system 40 such that a user (not shown) may interact with buttons, switches, touch screen display, or the like on the workstation 58 to facilitate operation of the mobile X-ray imaging system 40. The display 60 may be configured to display patient data and reconstructed X-ray images based upon X-ray image data. In an exemplary embodiment, the display 60 may be a touch-screen display. The operator workstation 58 may be configured to control operation of the vertical support column 46, horizontal support arm 48, X-ray source 50, collimator 52, X-ray detector 24, and/or input data (e.g., subject information), imaging related information (e.g., type of X-ray source, imaging techniques, imaging parameters, etc.) and/or perform image processing on acquired image data.

The base unit 42 also may include electronic circuitry, motors and power sources for powering and controlling the plurality of wheels 44, vertical support column 46, horizontal support arm 48, X-ray source 50, collimator 52, operator workstation 58 and display 60. A driving mechanism 64 is coupled to the base unit 42 for driving and maneuvering the mobile X-ray system 40. The horizontal support arm 48 may be moved vertically up and down along the vertical support column 46 to facilitate positioning of the X-ray source 50 and collimator 52 with respect to the subject 18 being imaged. Further, one or both of the vertical support column 46 and horizontal support arm 48 may be configured to allow rotation of the X-ray source 50 and collimator 52 about an axis. The X-ray source 50 and collimator 52 may be rotated to an appropriate position above the subject 18 in order to take an X-ray exposure of a region of interest of the subject 18. The subject 18 to be imaged may be located on a table 62, bed, gurney, stretcher, wheelchair or any other support during the X-ray exposure.

In an existing X-ray imaging system, a connector on the X-ray detector mates with a connector on the detector receptacle of a table or wall stand of a fixed X-ray imaging system, or the detector receptacle of a mobile X-ray imaging system. This connection provides power to the X-ray detector as well as communication between the detector and the X-ray imaging system.

In the present disclosure, the detector receptacles 26, 28 and 38 include a power source and/or a communication device providing a non-contact power interface for powering the detector 24 and/or a non-contact communication interface for providing communication between the X-ray imaging system 10, 40 and the detector 24. In an exemplary embodiment, the X-ray detector 24 may be inserted into a detector receptacle 26, 28 or 38 and a non-contact power interface may be used for charging a rechargeable battery in the detector 24 or providing power to the detector 24. In another exemplary embodiment, the X-ray detector 24 may be inserted into a detector receptacle 26, 28 or 38 and a non-contact communication interface may be used for providing communication between the X-ray imaging system 10, 40 and the detector 24. In a further exemplary embodiment, a combination of a non-contact power interface and a non-contact communication interface may be used for charging a rechargeable battery in the detector 24 or providing power to the detector 24, and providing communication between the X-ray imaging system 10, 40 and the detector 24.

Figure 3:
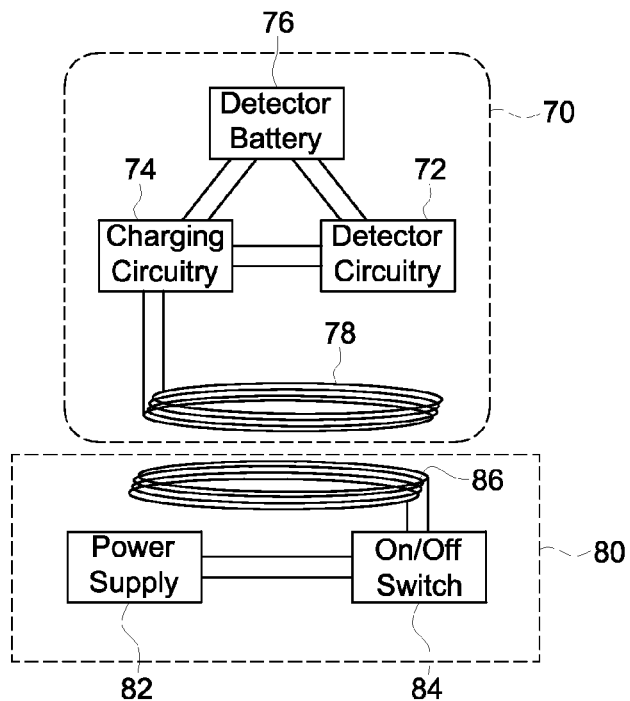
FIG. 3 is a block diagram of an exemplary embodiment of an X-ray detector inductively coupled to a power source.

FIG. 3 illustrates a block diagram of an exemplary embodiment of a portable wireless X-ray detector 70 inductively coupled to a power source 80 of an X-ray imaging system. In an exemplary embodiment, the power source 80 is coupled to a detector receptacle 26, 28 or 38, so that when an X-ray detector 70 is placed in a detector receptacle 26, 28 or 38, the detector 70 is in close proximity and inductively coupled to the power source 80, so that the power source 80 may be used for charging a detector battery 76 within the portable wireless X-ray detector 70. In an exemplary embodiment, the portable wireless X-ray detector 70 is a portable wireless digital X-ray detector. In an exemplary embodiment, the detector battery 76 is a rechargeable battery.

The X-ray detector 70 may include detector circuitry 72 coupled to a detector battery 76 and charging circuitry 74. The charging circuitry 74 is coupled to a receiver coil 78. The detector battery 76 powers the detector circuitry 72 during an imaging mode when the detector 70 is in the table detector receptacle 26 or wall stand detector receptacle 28, or during a digital cassette mode when the detector 70 is physically removed from the table detector receptacle 26, wall stand detector receptacle 28 or mobile detector receptacle 38. For example, the digital cassette mode may include imaging a subject in a bed, in a cross-table exam, in a wheelchair, or in any other non-table or non-wall stand imaging application.

In an exemplary embodiment, the detector circuitry 72 may include a detector panel and associated circuitry. For example, the detector panel may include a scintillator, transistor and photodiode array, and readout electronics. The associated circuitry may include AC to DC conversion circuitry, power regulation circuitry and control circuitry for controlling operation of the detector panel, charging circuitry 74 and detector battery 76. In an exemplary embodiment, the detector circuitry 72 may control the charging circuitry 74, and thus, charging of the detector battery 76.

The power source 80 may include a transmitter coil 86 coupled to an on/off switch 84 that is coupled to a power supply 82. In an exemplary embodiment, the on/off switch 84 is controlled by an X-ray imaging system state controller (not shown). When the on/off switch 84 is in an off position, the power supply 82 is decoupled from the transmitter coil 86, no current flows through the transmitter coil 86, and no magnetic field is generated in the transmitter coil 86. When the on/off switch 84 is in an on position, the power supply 82 is coupled to the transmitter coil 86, current flows through the transmitter coil 86, and a magnetic field is generated in the transmitter coil 86.

When the X-ray detector 70 is in the table detector receptacle 26, wall stand detector receptacle 28 or mobile detector receptacle 38, the detector 70 is located in close proximity to the power source 80. If the on/off switch 84 is in the on position, then the detector 70 is in a non-imaging charging mode. The power supply 82 is coupled to the transmitter coil 86, current flows through the transmitter coil 86, and a magnetic field is generated in the transmitter coil 86. The magnetic field generated in the transmitter coil 86 generates a voltage in the receiver coil 78, which provides current to the charging circuitry 74 to charge detector battery 76.

The inductive coupling between the transmitter coil 86 and receiver coil 78 eliminates a direct connection between the detector 70 and the table, wall stand or mobile X-ray imaging system. However, the inductive coils (transmitter coil 86 and receiver coil 78) may generate electromagnetic interference (EMI) in the detector 70 that may cause image artifacts on acquired images during image acquisition. Therefore, it is preferable to charge the detector battery 76 only during a non-imaging mode.

The imaging data acquired by the X-ray imaging system may be corrupted by various sources of EMI, such as the inductive coils in the X-ray detector 70 and power source 80. EMI of various frequencies and amplitudes may be superimposed on the acquired image data as it is collected, creating image artifacts on acquired images.

When the X-ray detector 70 is in the table detector receptacle 26, wall stand detector receptacle 28 or mobile detector receptacle 38, the detector 70 is located in close proximity to the power source 80. If the on/off switch 84 is in the off position, then the detector 70 is in an imaging mode and is powered by the detector battery 76 during an image acquisition. The power supply 82 is decoupled from the transmitter coil 86, no current flows through the transmitter coil 86, no magnetic field is generated in the transmitter coil 86, and no EMI is created by the transmitter coil 86 that could be received by the receiver coil 78. In addition, when the X-ray detector 70 is being used in a digital cassette mode, the detector is powered by the detector battery 76 and no EMI is generated from the transmitter coil 86 that could be received by the receiver coil 78.

In an exemplary embodiment, a wireless power receiver may be included in the detector and a wireless power transmitter may be included in the power source to provide wireless or non-contact power to the detector when being used in a digital cassette mode. Examples of commercial off-the-shelf wireless power receivers and transmitters include a Texas Instruments bq51013 wireless power receiver and a Texas Instruments bq500110 wireless power transmitter controller.

Figure 4A:
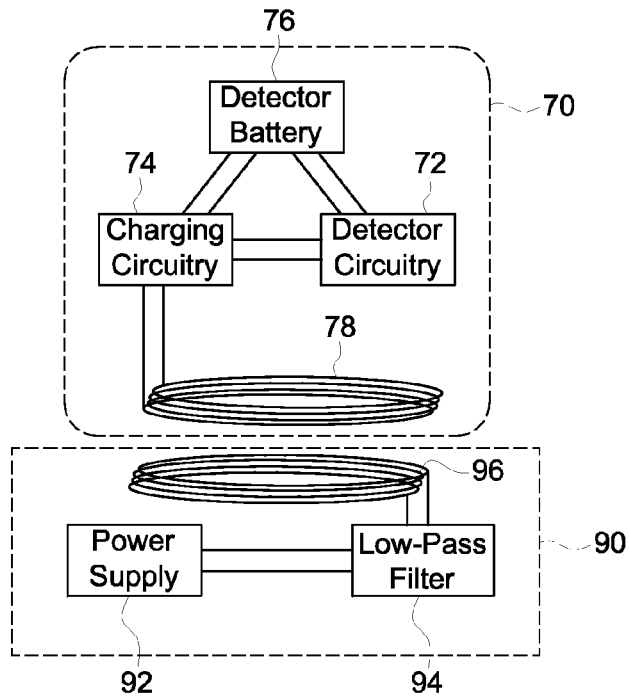
FIG. 4A is a block diagram of an exemplary embodiment of an X-ray detector inductively coupled to a power source.

FIG. 4A illustrates a block diagram of an exemplary embodiment of a portable wireless X-ray detector 70 inductively coupled to a power source 90 of an X-ray imaging system. In an exemplary embodiment, the power source 90 is coupled to a detector receptacle 26, 28 or 38, so that when an X-ray detector 70 is placed in a detector receptacle 26, 28 or 38, the detector 70 is in close proximity and inductively coupled to the power source 90, so that the power source 90 may be used for charging a detector battery 76 within the portable wireless X-ray detector 70. In an exemplary embodiment, the portable wireless X-ray detector 70 is a portable wireless digital X-ray detector. In an exemplary embodiment, the detector battery 76 is a rechargeable battery.

The X-ray detector 70 may include detector circuitry 72 coupled to a detector battery 76 and charging circuitry 74. The charging circuitry 74 is coupled to a receiver coil 78. The detector battery 76 powers the detector circuitry 72 during an imaging mode when the detector 70 is in the table detector receptacle 26 or wall stand detector receptacle 28, or during a digital cassette mode when the detector 70 is physically removed from the table detector receptacle 26, wall stand detector receptacle 28 or mobile detector receptacle 38.

In an exemplary embodiment, the detector circuitry 72 may include a detector panel and associated circuitry. For example, the detector panel may include a scintillator, transistor and photodiode array, and readout electronics. The associated circuitry may include AC to DC conversion circuitry, power regulation circuitry and control circuitry for controlling operation of the detector panel, charging circuitry 74 and detector battery 76. In an exemplary embodiment, the detector circuitry 72 may control the charging circuitry 74, and thus, charging of the detector battery 76.

The power source 90 may include a transmitter coil 96 coupled to a signal filter device, such as a low-pass filter 94 that is coupled to a power supply 92. In an exemplary embodiment, the low-pass filter 94 is designed to pass low frequency signals, preferably signals less than 10 kHz, but attenuate signals with frequencies greater than 10 kHz. The power supply 92 supplies a signal to the low-pass filter 94 that filters the signal and supplies a low frequency signal, preferably less than 10 kHz, to the transmitter coil 96. The power supply 92 is configured to drive the transmitter coil 96 at a fundamental frequency that is lower than the low-pass filter pass band. This low frequency signal generates a magnetic field in the transmitter coil 96.

The inductive coupling between the transmitter coil 96 and receiver coil 78 eliminates a direct connection between the detector 70 and the table, wall stand or mobile X-ray imaging system. When the X-ray detector 70 is in the table detector receptacle 26, wall stand detector receptacle 28 or mobile detector receptacle 38, the detector 70 is located in close proximity to the power source 90. The magnetic field generated in the transmitter coil 96 generates a voltage in the receiver coil 78, which provides current to the charging circuitry 74 to charge detector battery 76. The fundamental frequency of the signal from the power supply is low enough to not cause any EMI in the detector 70 that may cause image artifacts on acquired images during image acquisition. In an exemplary embodiment, it is preferable to charge the detector battery 76 with a low frequency power supply signal, preferable less than 10 kHz, and having a low-pass filter 94 that is designed to eliminate all harmonics from the fundamental frequency of the low frequency power supply signal.

Figure 4B:
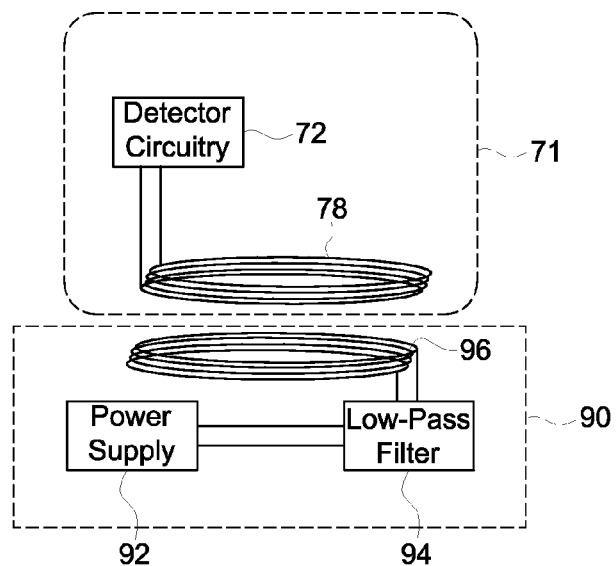
FIG. 4B is a block diagram of an exemplary embodiment of an X-ray detector inductively coupled to a power source.

FIG. 4B illustrates a block diagram of an exemplary embodiment of a portable wireless X-ray detector 71 inductively coupled to a power source 90 of an X-ray imaging system. The X-ray detector 71 may include detector circuitry 72 coupled to a receiver coil 78. In an exemplary embodiment, the detector circuitry 72 may include a detector panel and associated circuitry. For example, the detector panel may include a scintillator, transistor and photodiode array, and readout electronics. The associated circuitry may include AC to DC conversion circuitry, power regulation circuitry and control circuitry for controlling operation of the detector panel and power conversion and regulation circuitry. The power source 90 may include a transmitter coil 96 coupled to a signal filter device, such as a low-pass filter 94 that is coupled to a power supply 92. The low-pass filter 94 is designed to pass low frequency signals, preferably signals less than 10 kHz, but attenuate signals with frequencies greater than 10 kHz. The power supply 92 supplies a signal to the low-pass filter 94 that filters the signal and supplies a low frequency signal, preferably less than 10 kHz, to the transmitter coil 96. The power supply 92 is configured to drive the transmitter coil 96 at a fundamental frequency that is lower than the low-pass filter pass band. This low frequency signal generates a magnetic field in the transmitter coil 96. The inductive coupling between the transmitter coil 96 and receiver coil 78 eliminates a direct connection between the detector 71 and the table, wall stand or mobile X-ray imaging system. When the X-ray detector 71 is in the table detector receptacle 26, wall stand detector receptacle 28 or mobile detector receptacle 38, the detector 71 is located in close proximity to the power source 90. The magnetic field generated in the transmitter coil 96 generates a voltage in the receiver coil 78, which provides current to the detector circuitry 72 for powering the detector circuitry 72. The fundamental frequency of the signal from the power supply is low enough to not cause any EMI in the detector 71 that may cause image artifacts on acquired images during image acquisition. Therefore, it is preferable to power the detector circuitry 72 with a low frequency power supply signal, preferable less than 10 kHz, and having a low-pass filter 94 that is designed to eliminate all harmonics from the fundamental frequency of the low frequency power supply signal. In an exemplary embodiment, the power source 90 may be used to power the detector circuitry 72 directly with the low frequency power source. Therefore, the charging circuitry 74 and detector battery 76 are not needed and deleted from the embodiment shown in FIG. 4B.

Figure 5A:
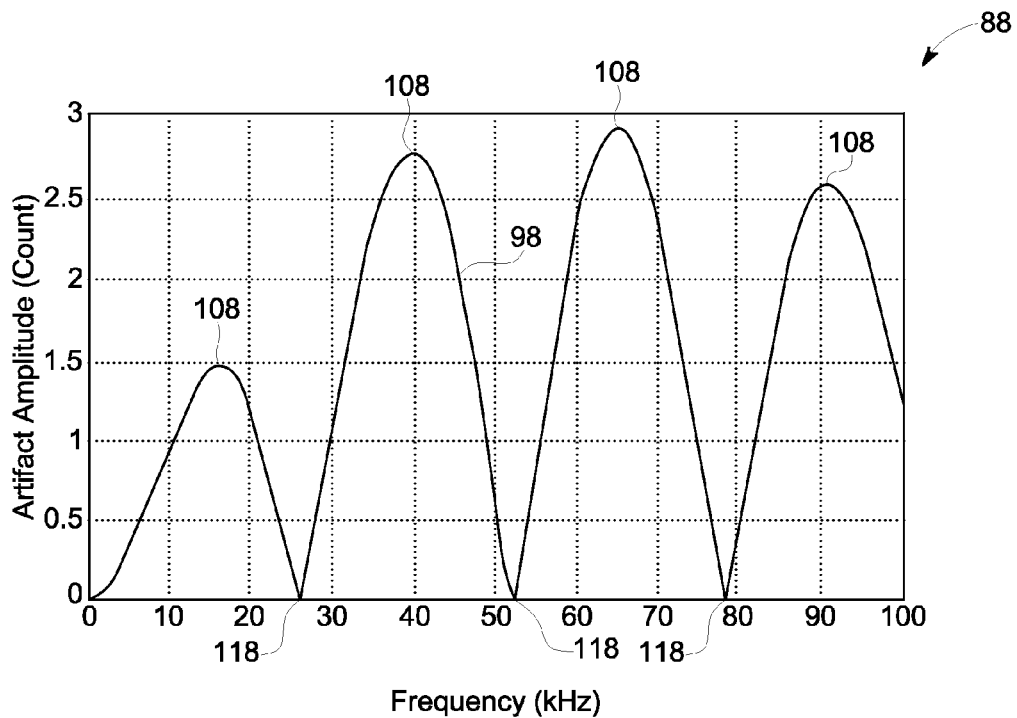
FIG. 5A is a graphical diagram of an exemplary embodiment of a method of eliminating the effects of electromagnetic interference (EMI) on an X-ray detector.

Generally, an X-ray detector is very sensitive to some EMI frequencies, but not sensitive to other EMI frequencies. The non-sensitive EMI frequencies are called null frequencies. Testing was conducted to determine these null frequencies for an X-ray detector. The results of the testing is shown in FIG. 5A. FIG. 5A illustrates an exemplary embodiment of a graph 88 showing the relationship between EMI image artifact amplitude on the vertical y-axis versus EMI frequency on the horizontal x-axis. The EMI curve 98 has peaks 108 where the EMI image artifact amplitude is largest for a particular frequency and nulls 118 where the EMI image artifact amplitude is lowest, in fact zero, for a particular frequency (null frequencies). The null frequencies correspond to frequencies at which the X-ray detector is immune to EMI. Therefore, the null frequencies are the frequencies to be selected as the operating frequencies of inductive coupling in order to avoid EMI image artifacts on acquired images during image acquisition.

Figure 5B:
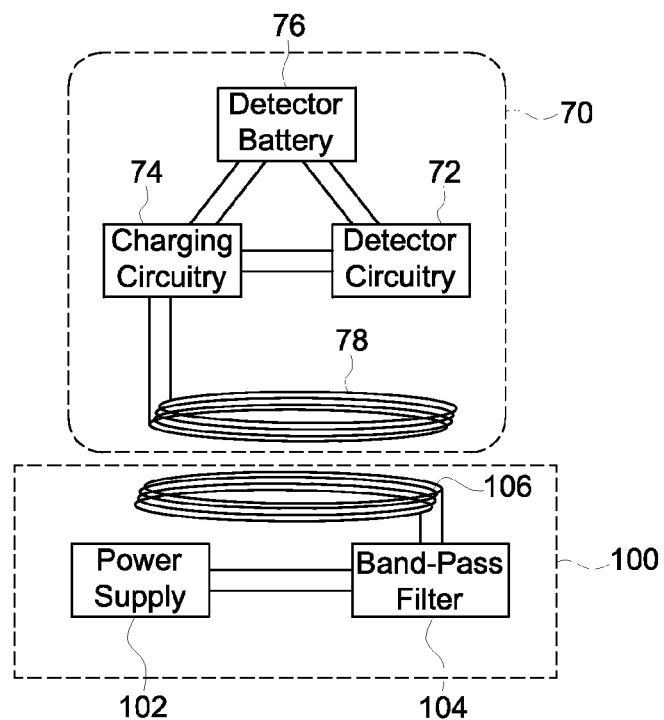
FIG. 5B is a block diagram of an exemplary embodiment of an X-ray detector inductively coupled to a power source.

FIG. 5B illustrates a block diagram of an exemplary embodiment of a portable wireless X-ray detector 70 inductively coupled to a power source 100 of an X-ray imaging system. In an exemplary embodiment, the power source 100 is coupled to a detector receptacle 26, 28 or 38, so that when an X-ray detector 70 is placed in a detector receptacle 26, 28 or 38, the detector 70 is in close proximity and inductively coupled to the power source 100, so that the power source 100 may be used for charging a detector battery 76 within the portable wireless X-ray detector 70. In an exemplary embodiment, the portable wireless X-ray detector 70 is a portable wireless digital X-ray detector. In an exemplary embodiment, the detector battery 76 is a rechargeable battery.

The X-ray detector 70 may include detector circuitry 72 coupled to a detector battery 76 and charging circuitry 74. The charging circuitry 74 is coupled to a receiver coil 78. The detector battery 76 powers the detector circuitry 72 during an imaging mode when the detector 70 is in the table detector receptacle 26 or wall stand detector receptacle 28, or during a digital cassette mode when the detector 70 is physically removed from the table detector receptacle 26, wall stand detector receptacle 28 or mobile detector receptacle 38.

In an exemplary embodiment, the detector circuitry 72 may include a detector panel and associated circuitry. For example, the detector panel may include a scintillator, transistor and photodiode array, and readout electronics. The associated circuitry may include AC to DC conversion circuitry, power regulation circuitry and control circuitry for controlling operation of the detector panel, charging circuitry 74 and detector battery 76. In an exemplary embodiment, the detector circuitry 72 may control the charging circuitry 74, and thus, charging of the detector battery 76.

The power source 100 may include a transmitter coil 106 coupled to a signal filter device, such as a band-pass filter 104 that is coupled to a power supply 102. In an exemplary embodiment, the band-pass filter 104 is designed to pass a null frequency signal. A null frequency signal is a signal having a frequency where the EMI image artifact amplitude is zero as shown in FIG. 5A. The power supply 102 supplies a signal to the band-pass filter 104 that filters the signal and supplies a null frequency signal to the transmitter coil 106. The power supply 102 is configured to drive the transmitter coil 106 at a fundamental frequency that is within the band-pass filter 104 pass band. This null frequency signal generates a magnetic field in the transmitter coil 106. The fundamental frequency of the signal from the power supply 102 is selected to be one of the null frequencies, which the band-pass filter 104 passes and eliminates all other frequencies from the signal.

The inductive coupling between the transmitter coil 106 and receiver coil 78 eliminates a direct connection between the detector 70 and the table, wall stand or mobile X-ray imaging system. When the X-ray detector 70 is in the table detector receptacle 26, wall stand detector receptacle 28 or mobile detector receptacle 38, the detector 70 is located in close proximity to the power source 100. The magnetic field generated in the transmitter coil 106 generates a voltage in the receiver coil 78, which provides current to the charging circuitry 74 to charge detector battery 76. The frequency of the signal from the power supply and the pass band frequency of the band-pass filter are both selected to be one and the same one of the null frequencies to not cause any EMI in the detector 70 that may cause image artifacts on acquired images during image acquisition. In an exemplary embodiment, it is preferable to charge the detector battery 76 with a power supply signal having a null frequency that does not generate any EMI in the detector 70.

Figure 5C:
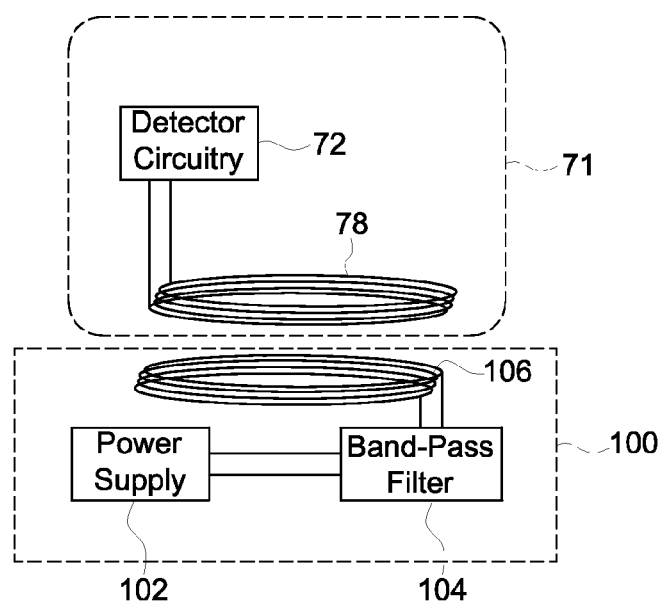
FIG. 5C is a block diagram of an exemplary embodiment of an X-ray detector inductively coupled to a power source.

FIG. 5C illustrates a block diagram of an exemplary embodiment of a portable wireless X-ray detector 71 inductively coupled to a power source 100 of an X-ray imaging system. The X-ray detector 71 may include detector circuitry 72 coupled to a receiver coil 78. In an exemplary embodiment, the detector circuitry 72 may include a detector panel and associated circuitry. For example, the detector panel may include a scintillator, transistor and photodiode array, and readout electronics. The associated circuitry may include AC to DC conversion circuitry, power regulation circuitry and control circuitry for controlling operation of the detector panel and power conversion and regulation circuitry. The power source 100 may include a transmitter coil 106 coupled to a signal filter device, such as a band-pass filter 104 that is coupled to a power supply 102. The power supply 102 is configured to drive the transmitter coil 106 at a fundamental frequency that is within the band-pass filter 104 pass band. The band-pass filter 104 is designed to pass a null frequency signal. A null frequency signal is a signal having a frequency where the EMI image artifact amplitude is zero as shown in FIG. 5A. The fundamental frequency of the signal from the power supply 102 is selected to be one of the null frequencies, which the band-pass filter 104 passes and eliminates all other frequencies from the signal. This null frequency signal generates a magnetic field in the transmitter coil 106.

The inductive coupling between the transmitter coil 106 and receiver coil 78 eliminates a direct connection between the detector 71 and the table, wall stand or mobile X-ray imaging system. When the X-ray detector 71 is in the table detector receptacle 26, wall stand detector receptacle 28 or mobile detector receptacle 38, the detector 71 is located in close proximity to the power source 90. The magnetic field generated in the transmitter coil 106 generates a voltage in the receiver coil 78, which provides current to the detector circuitry 72 for powering the detector circuitry 72. The frequency of the signal from the power supply and the pass band frequency of the band-pass filter are both selected to be one and the same one of the null frequencies to not cause any EMI in the detector 71 that may cause image artifacts on acquired images during image acquisition. In an exemplary embodiment, the power source 100 may be used to power the detector circuitry 72 directly with the selected null frequency power source. Therefore, the charging circuitry 74 and detector battery 76 are not needed and deleted from the embodiment shown in FIG. 5C.

Figure 6A:
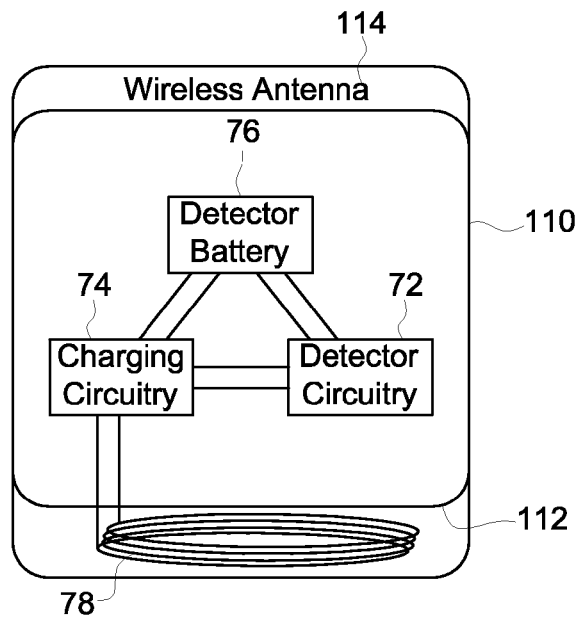
FIG. 6A is a block diagram of an exemplary embodiment of a shielded X-ray detector.
Figure 6B:
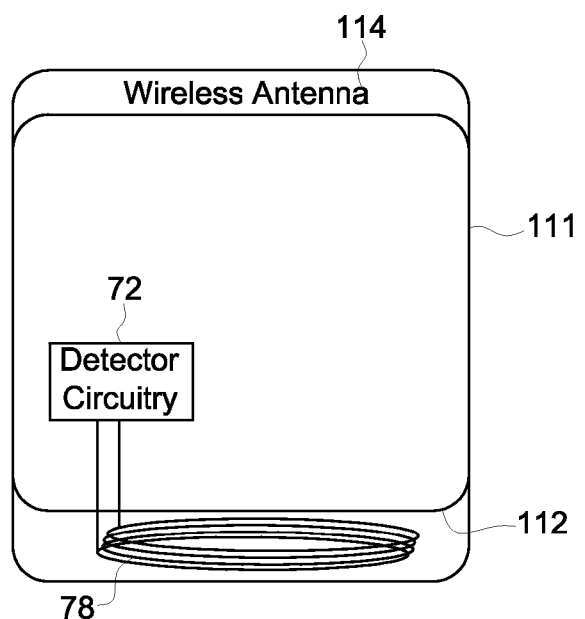
FIG. 6B is a block diagram of an exemplary embodiment of a shielded X-ray detector.

In order to improve the electromagnetic compatibility (EMC) performance of a portable wireless X-ray detector, it is desirable to reduce or eliminate the unwanted effects of EMI from the portable wireless X-ray detector. One way of doing this is to electrically shield the detector circuitry within the X-ray detector from any EMI producing devices. FIGS. 6A and 6B illustrate block diagrams of exemplary embodiments of shielded digital X-ray detectors 110 and 111. The X-ray detector 110 or 111 may be divided into three sections. A first section may include a wireless antenna 114; a second section may include one or more receiver coils 78; and a third section may include detector circuitry 72. In particular, the shielded X-ray detector 110 in FIG. 6A includes detector circuitry 72 coupled to a detector battery 76 and charging circuitry 74. The charging circuitry 74 is coupled to a receiver coil 78. The detector battery 76 is used to power the detector circuitry 72. In an exemplary embodiment, the detector circuitry 72, detector battery 76 and charging circuitry 74 may be electrically shielded from the wireless antenna 114 and the one or more receiver coils 78 by a conductive material or conductive member 112 that provides EMI shielding from the wireless antenna 114 and the one or more receiver coils 78. EMI shielding protecting the detector circuitry 72, detector battery 76 and charging circuitry 74 from EMI. As shown in FIG. 6B, the detector circuitry 72 may be electrically shielded from the one or more receiver coils 78 by a conductive material or conductive member 112. In this embodiment, an inductively coupled power source may be used to power the detector circuitry 72 directly. Therefore, the charging circuitry 74 and detector battery 76 are not needed. EMI shielding protects the detector circuitry 72 from EMI. In yet another exemplary embodiment, the one or more receiver coils 78 may be electrically shielded from the detector circuitry 72 by a conductive material or conductive member 112 that provides EMI shielding from the one or more receiver coils 78. Because the detector circuitry 72 is electrically shielded from the one or more receiver coils 78 by a conductive material or conductive member 112, the detector circuitry 72 is immune from EMI, and therefore, the detector battery 76 may be charged or power provided directly to the detector circuitry 72 through inductive coupling.

The wireless antenna 114 may operate with 802.11 or UWB wireless communication. IEEE 802.11 is a set of standards for implementing wireless local area network (WLAN) computer communication in the 2.4, 3.6 and 5 GHz frequency bands. They are created and maintained by the IEEE LAN/MAN Standards Committee (IEEE 802). The base version of the standard IEEE 802.11-2007 has had subsequent amendments. These standards provide the basis for wireless network products using the Wi-Fi brand. The 802.11 family consists of a series of over-the-air modulation techniques that use the same basic protocol. The most popular are those defined by the 802.11b and 802.11g protocols, which are amendments to the original standard. 802.11-1997 was the first wireless networking standard, but 802.11b was the first widely accepted one, followed by 802.11g and 802.11n. 802.11n is a new multi-streaming modulation technique. Other standards in the family (c-f, h, j) are service amendments and extensions or corrections to the previous specifications. Ultra-wideband (also known as UWB, ultra-wide band and ultraband) is a radio technology pioneered by Robert A. Scholtz and others which may be used at a very low energy level for short-range, high-bandwidth communications using a large portion of the radio spectrum. UWB has traditional applications in non-cooperative radar imaging. Most recent applications target sensor data collection, precision locating and tracking applications similar to spread spectrum, UWB communications transmit in a way which does not interfere with conventional narrowband and carrier wave uses in the same frequency band. Unlike spread spectrum, however, ultra-wideband does not employ frequency-hopping. Ultra-wideband is a technology for transmitting information spread over a large bandwidth (>500 MHz); this should, in theory and under the right circumstances, be able to share spectrum with other users. Regulatory settings by the Federal Communications Commission (FCC) in the United States intend to provide an efficient use of radio bandwidth while enabling high-data-rate personal area network (PAN) wireless connectivity; longer-range, low-data-rate applications; and radar and imaging systems.

Figure 7A:
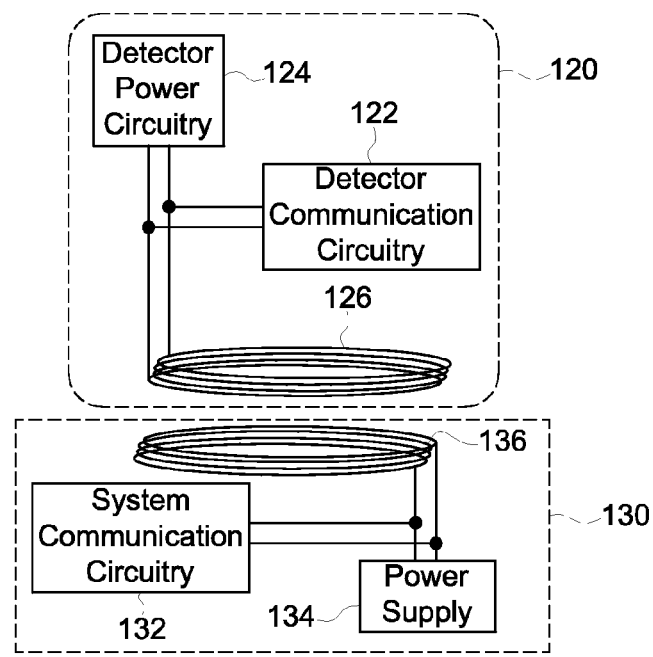
FIG. 7A is a block diagram of an exemplary embodiment of an X-ray detector inductively coupled to a power source and communication device.
Figure 7B:
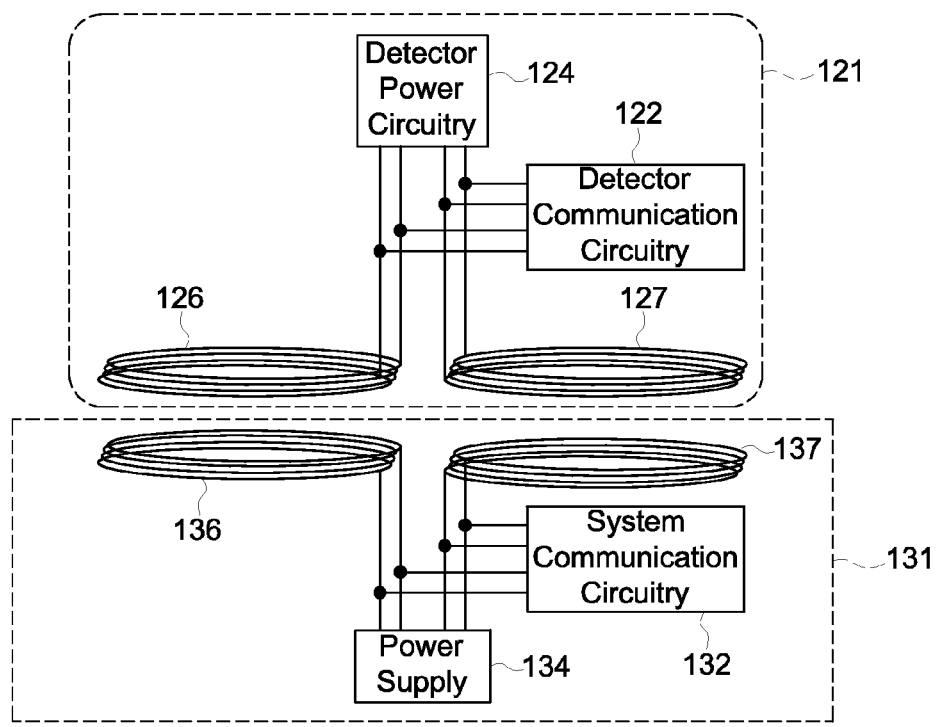
FIG. 7B is a block diagram of an exemplary embodiment of an X-ray detector inductively coupled to a power source and communication device.

FIGS. 7A and 7B illustrate block diagrams of exemplary embodiments of a portable wireless X-ray detector 120, 121 inductively coupled to a power source and communication device 130, 131 of an X-ray imaging system. In an exemplary embodiment, the power source and communication device 130, 131 is coupled to a detector receptacle 26, 28 or 38, so that when an X-ray detector 120, 121 is placed in a detector receptacle 26, 28 or 38, the detector 120, 121 is in close proximity to the power source and communication device 130, 131, so that the power source and communication device 130, 131 may be used for non-contact powering of the portable wireless X-ray detector 120, 121 and/or providing wireless communication between the detector 120, 121 and the X-ray imaging system.

Referring to FIG. 7A, the X-ray detector 120 includes detector circuitry (not shown) coupled to detector power circuitry 124 and detector communication circuitry 122. The detector power circuitry 124 and detector communication circuitry 122 may be coupled to a receiver coil 126. The power source and communication device 130 may include a transmitter coil 136 coupled to system communication circuitry 132 and a power supply 134. The power supply 134 supplies a power signal to the transmitter coil 136. The system communication circuitry 132 provides a communication signal that is modulated on the power signal from the power supply 134. In an exemplary embodiment, the X-ray detector 120 is a portable wireless digital X-ray detector.

The inductive coupling between the transmitter coil 136 and receiver coil 126 eliminates a direct connection between the detector 120 and the table, wall stand or mobile X-ray imaging system. However, the inductive coupling provides a wireless non-contact power and communication path between the power source and communication device 130 and the detector 120. When the X-ray detector 120 is in the table detector receptacle 26, wall stand detector receptacle 28 or mobile detector receptacle 38, the detector 120 is located in close proximity to the power source and communication device 130. The power signal and modulated communication signal generates a magnetic field in the transmitter coil 136. This magnetic field in the transmitter coil 136 generates a voltage in the receiver coil 126 through inductive coupling, which provides the power signal to the detector power circuitry 124 to power the detector 120 and the communication signal to the detector communication circuitry 122. In an exemplary embodiment, the communication signal is demodulated from the power signal within the X-ray detector 120 by the detector communication circuitry 122.

Referring to FIG. 7B, more than one pair of coils may be used. In particular, the X-ray imaging system power source and communication device 131 may include a transmitter coil 136 and a receiver coil 137 coupled to the system communication circuitry 132 and power supply 134. Also, the X-ray detector 121 may include a detector receiving coil 126 and a detector transmitting coil 127 coupled to the detector communication circuitry 122 and detector power circuitry 124. Communication from the X-ray imaging system power source and communication device 131 to the detector 121 is modulated over a signal between the transmitter coil 136 and receiver coil 126, and communication from the detector 121 to the X-ray imaging system power source and communication device 131 is modulated over a signal between the detector transmitter coil 127 and receiver coil 137.

In an exemplary embodiment, the detector power circuitry 124 may include charging circuitry and a rechargeable battery (not shown) for powering the detector 120, 121 or AC to DC conversion circuitry and power regulation circuitry (not shown) for powering the detector 120, 121. In an exemplary embodiment, a battery and wireless transceiver may be included in the X-ray detector 120, 121 to provide wireless communication when the detector 120, 121 is being used in a digital cassette mode.

Figure 8:
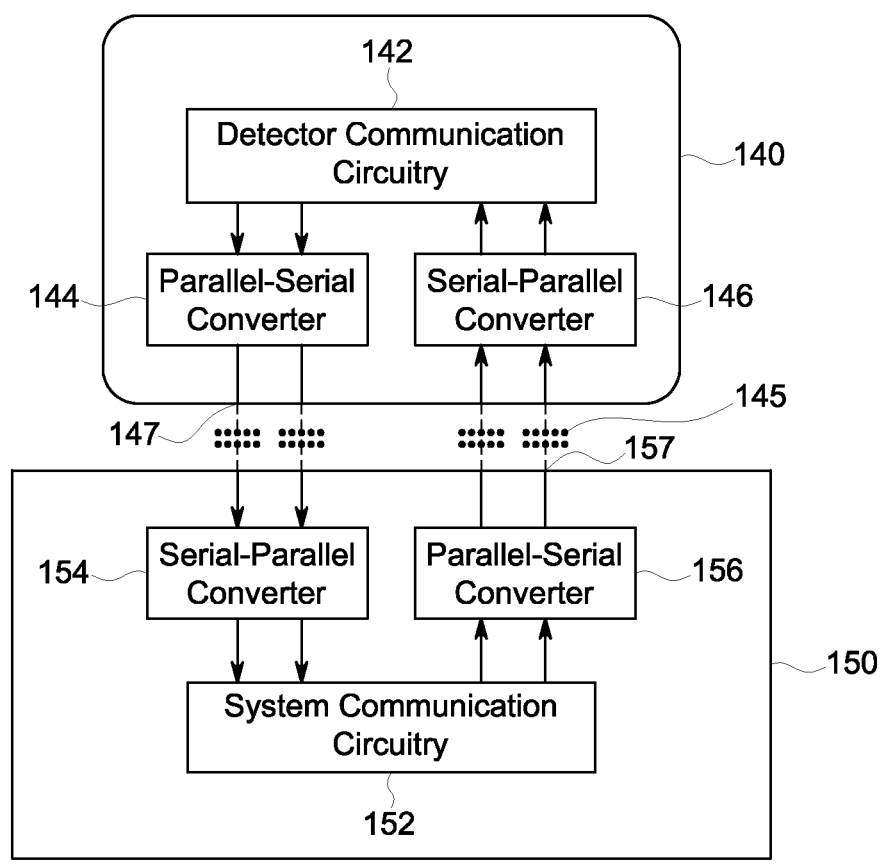
FIG. 8 is a block diagram of an exemplary embodiment of an X-ray detector capacitively coupled to a communication device.

FIG. 8 illustrates a block diagram of an exemplary embodiment of a portable wireless X-ray detector 140 capacitively coupled to a communication device 150 of an X-ray imaging system. In an exemplary embodiment, the communication device 150 is coupled to a detector receptacle 26, 28 or 38, so that when an X-ray detector 140 is placed in a detector receptacle 26, 28 or 38, the detector 140 is in close proximity to the communication device 150, so that the communication device 150 may be used for non-contact wireless communication between the detector 140 and the X-ray imaging system. In an exemplary embodiment, the X-ray detector 140 may include detector circuitry (not shown) and detector power circuitry (not shown) coupled to the detector communication circuitry 142. The X-ray detector 140 may include a plurality of conductive plates 147 coupled to a sidewall of the portable wireless X-ray detector 140. In addition, the communication device 150 may include a plurality of conductive plates 157 coupled to a sidewall of the communication device 150. When the plurality of conductive plates 147, 157 are in close proximity to one another, they form capacitors 145 between the detector 140 and communication device 150.

In the embodiment shown, the X-ray detector 140 includes detector communication circuitry 142 coupled to a parallel to serial converter 144 and a serial to parallel converter 146, which are coupled to the plurality of conductive plates 147 coupled to a sidewall of the portable wireless X-ray detector 140. The communication device 150 may include system communication circuitry 152 coupled to a serial to parallel converter 154 and a parallel to serial converter 156, which are coupled to the plurality of conductive plates 157 coupled to a sidewall of the communication device 150. The plurality of conductive plates 147, 157 form capacitors 145 between the detector 140 and communication device 150 when the conductive plates 147 of the detector 140 are in close proximity with the conductive plates 157 of the communication device 150.

The capacitive coupling between the communication device 150 and detector 140 eliminates a direct connection between the detector 140 and the table, wall stand or mobile X-ray imaging system. However, the capacitive coupling provides a wireless non-contact communication path between the communication device 150 and the detector 140. When the X-ray detector 140 is in the table detector receptacle 26, wall stand detector receptacle 28 or mobile detector receptacle 38, the detector 140 is located in close proximity to the communication device 150. Communication and data from the system communication circuitry 152 of the communication device 150 passes through the parallel to serial converter 156 in the communication device 150 through conductive plates 157, 147 of capacitors 145 to the serial to parallel converter 146 and detector communication circuitry 142 in detector 140. In return, communication and data from the detector communication circuitry 142 of the detector 140 passes through the parallel to serial converter 144 in the detector 140 through conductive plates 147, 157 of capacitors 145 to the serial to parallel converter 154 and system communication circuitry 152 in communication device 150.

Figure 9:
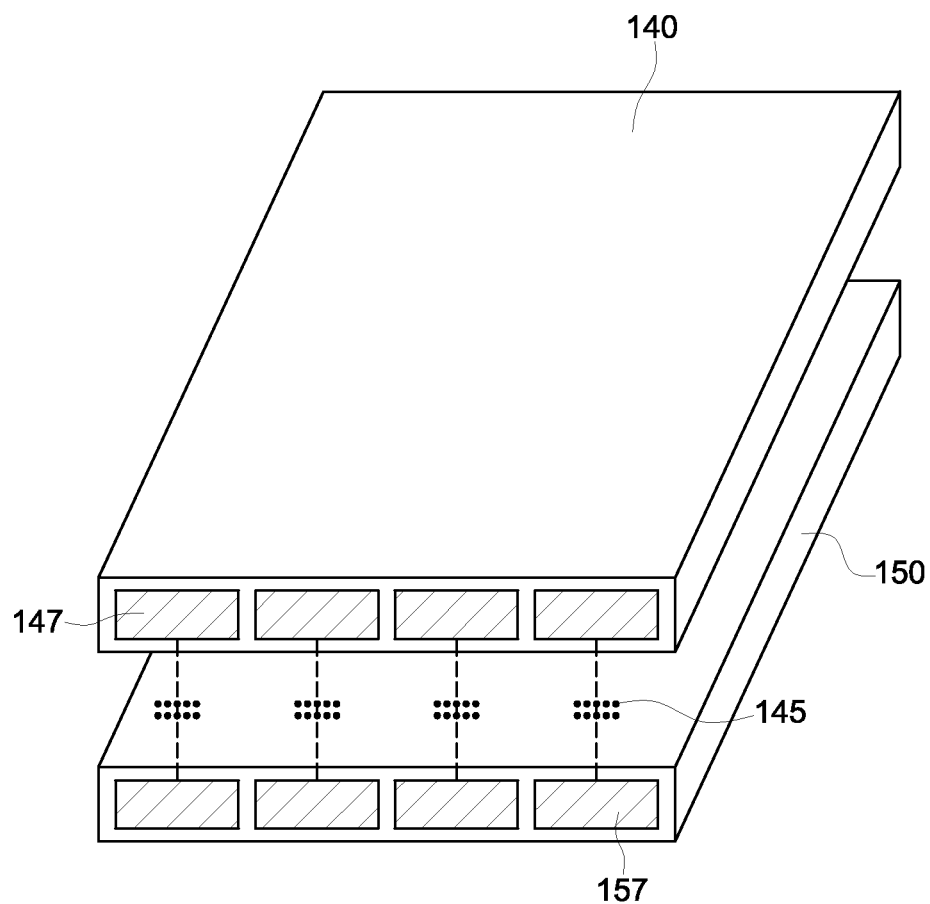
FIG. 9 is a schematic diagram of an exemplary embodiment of an X-ray detector capacitively coupled to a communication device.

FIG. 9 illustrates a schematic diagram of an exemplary embodiment of the capacitive coupling between the portable wireless X-ray detector 140 and the communication device 150. In this embodiment, each capacitor 145 comprises a pair of conductive plates 147, 157 coupled to the ends or sides of the portable wireless X-ray detector 140 and the communication device 150.

When the X-ray detector 140 is in the table detector receptacle 26, wall stand detector receptacle 28 or mobile detector receptacle 38, the conductive plates 147, 157 are in close proximity to one another forming capacitors 145 between the detector 140 and the communication device 150. In an exemplary embodiment, the conductive plates 147, 157 may be positioned on any end or side of the portable wireless X-ray detector 140 and the communication device 150, such that they are in close proximity to one another forming capacitors 145 when the X-ray detector 140 is located in the table detector receptacle 26, wall stand detector receptacle 28 or mobile detector receptacle 38.

The capacitive coupling provides a non-contact communication path between the detector and the X-ray imaging system, similar to wireless communication. The difference is that the capacitive coupling has a much higher communication speed due to the very short distance between the capacitive plates. For example, wireless communication can provide 20-80 Mbps throughput, while capacitive coupling can provide over 1 Gbps throughput.

Figure 10A:
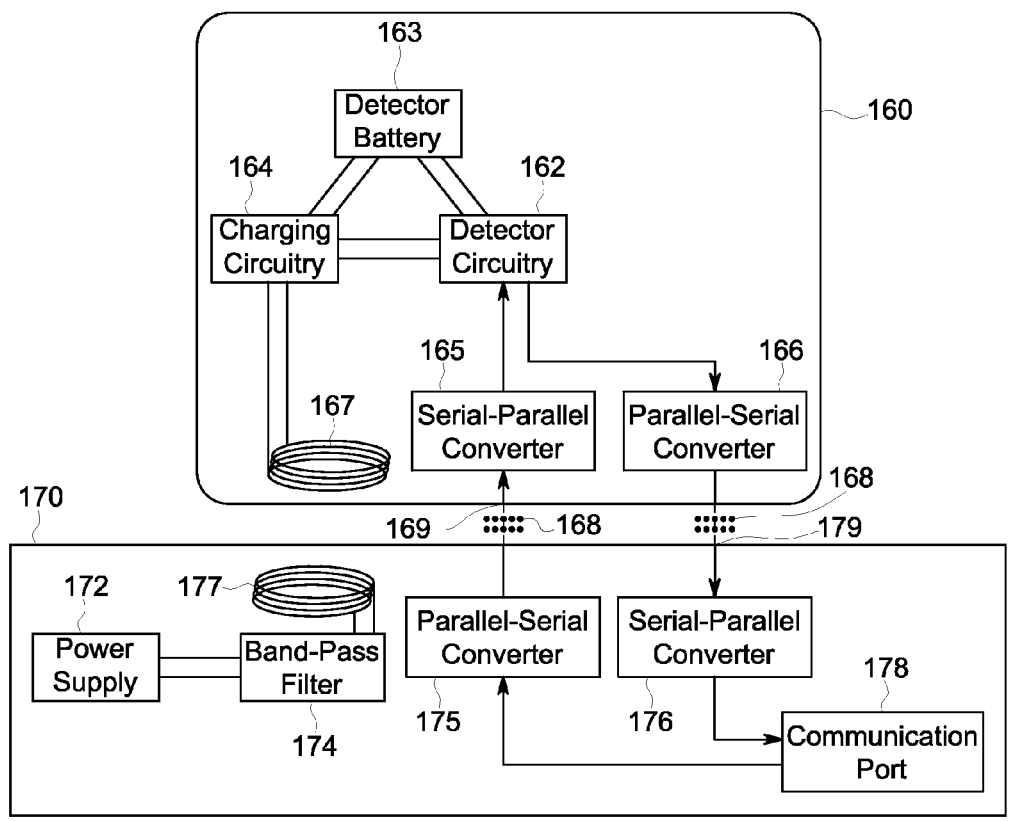
FIG. 10A is a block diagram of an exemplary embodiment of an X-ray detector inductively and capacitively coupled to a power source and communication device.

FIG. 10A illustrates a block diagram of an exemplary embodiment of a portable wireless X-ray detector 160 inductively and capacitively coupled to a power source and communication device 170 of an X-ray imaging system. FIG. 10A includes both inductive power coupling and capacitance communication coupling. In an exemplary embodiment, the power source and communication device 170 is coupled to a detector receptacle 26, 28 or 38. When the X-ray detector 160 is placed in a detector receptacle 26, 28 or 38, the detector 160 is in close proximity to the power source and communication device 170. The power source and communication device 170 may be used for non-contact powering of the portable wireless X-ray detector 160 and/or providing wireless communication between the detector 160 and the X-ray imaging system.

The X-ray detector 160 may include detector circuitry 162 coupled to a detector battery 163 and charging circuitry 164. The charging circuitry 164 is coupled to a receiver coil 167. The detector battery 163 is used to power the detector circuitry 162 during an imaging mode when the detector 160 is in the table detector receptacle 26 or wall stand detector receptacle 28, or during a digital cassette mode when the detector 160 is physically removed from the table detector receptacle 26, wall stand detector receptacle 28 or mobile detector receptacle 38. In an exemplary embodiment, the detector battery 163 is a rechargeable battery. The X-ray detector 160 may include conductive plates 169 coupled to a sidewall of the detector 160. The detector circuitry 162 is further coupled to a serial to parallel converter 165 and a parallel to serial converter 166. The serial to parallel converter 165 and the parallel to serial converter 166 are coupled to the conductive plates 169 and used to provide a capacitively coupled communication path between the detector 160 and the power source and communication device 170.

The power source and communication device 170 may include a transmitter coil 177 coupled to a band-pass filter 174 that is coupled to a power supply 172. In an exemplary embodiment, the band-pass filter 174 is designed to pass a null frequency signal. The power supply 172 supplies a signal to the band-pass filter 174 that filters the signal and supplies a null frequency signal to the transmitter coil 177. The power supply 172 is configured to drive the transmitter coil 177 at a fundamental frequency (null frequency) that is within the band-pass filter 174 pass band. The power source and communication device 170 may further include a communication port 178 coupled to a parallel to serial converter 175 and a serial to parallel converter 176. The power source and communication device 170 may include conductive plates 179 coupled to a sidewall of the power source and communication device 170. The parallel to serial converter 175 and serial to parallel converter 176 are coupled to the conductive plates 179 and used to provide a capacitively coupled communication path between the power source and communication device 170 and the detector 160.

When the conductive plates 169, 179 are in close proximity to one another, they form capacitors 168 between the detector 160 and power source and communication device 170. Communication and data from the communication port 178 of the power source and communication device 170 passes through the parallel to serial converter 175 in the power source and communication device 170 through capacitors 168 to the serial to parallel converter 165 and detector circuitry 162 in detector 160. In return, communication and data from the detector circuitry 162 of the detector 160 passes through the parallel to serial converter 166 in the detector 160 through capacitors 168 to the serial to parallel converter 176 and communication port 178 in the power source and communication device 170.

Inductive coupling between the transmitter coil 177 and receiver coil 167 eliminates a direct connection between the detector 160 and the table, wall stand or mobile X-ray imaging system. The inductive coupling provides a wireless non-contact power path between the power source and communication device 170 and the detector 160 for charging the detector battery 163.

Capacitive coupling between the power source and communication device 170 and detector 160 eliminates a direct connection between the detector 160 and the table, wall stand or mobile X-ray imaging system. The capacitive coupling provides a wireless non-contact communication path between the power source and communication device 170 and the detector 160 for providing communication and data transfer between the power source and communication device 170 and the detector 160.

Figure 10B:
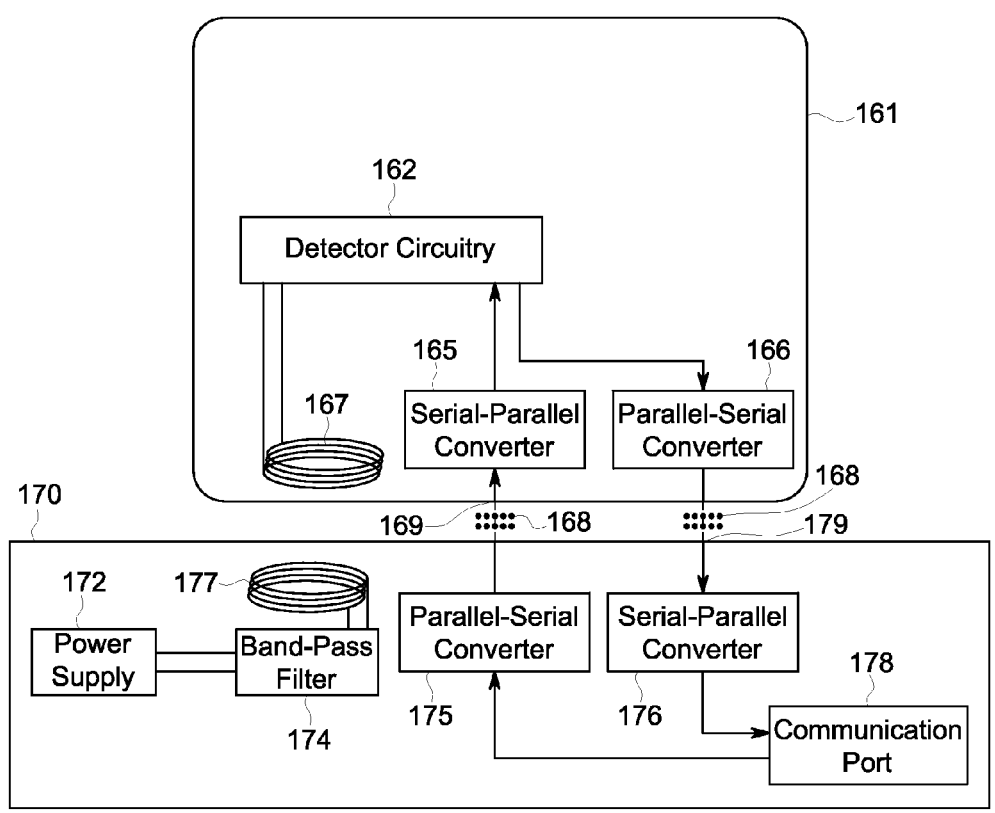
FIG. 10B is a block diagram of an exemplary embodiment of an X-ray detector inductively and capacitively coupled to a power source and communication device.

FIG. 10B illustrates a block diagram of an exemplary embodiment of a portable wireless X-ray detector 161 inductively and capacitively coupled to a power source and communication device 170 of an X-ray imaging system. The X-ray detector 161 may include detector circuitry 162 coupled to a receiver coil 167, a serial to parallel converter 165, and a parallel to serial converter 166. The serial to parallel converter 165 and parallel to serial converter 166 are coupled to conductive plates 169 that are coupled to a sidewall of the detector 161 to provide a capacitively coupled communication path between the detector 161 and the power source and communication device 170.

In an exemplary embodiment, the detector circuitry 162 may include a detector panel and associated circuitry. For example, the detector panel may include a scintillator, transistor and photodiode array, and readout electronics. The associated circuitry may include AC to DC conversion circuitry, power regulation circuitry and control circuitry for controlling operation of the detector panel and power conversion and regulation circuitry.

The power source and communication device 170 may include a transmitter coil 177 coupled to a band-pass filter 174 that is coupled to a power supply 172. In an exemplary embodiment, the power supply 172 is designed to generate and the band-pass filter 174 is designed to pass the same null frequency signal. The power supply 172 supplies a signal to the band-pass filter 174 that filters the signal and supplies a null frequency signal to the transmitter coil 177. The power supply 172 is configured to drive the transmitter coil 177 at a fundamental frequency (null frequency) that is within the band-pass filter 174 pass band. The power source and communication device 170 may further include a communication port 178 coupled to a parallel to serial converter 175 and a serial to parallel converter 176. The power source and communication device 170 may include conductive plates 179 coupled to a sidewall of the power source and communication device 170. The parallel to serial converter 175 and serial to parallel converter 176 are coupled to the conductive plates 179 and used to provide a capacitively coupled communication path between the power source and communication device 170 and the detector 161. When the conductive plates 169, 179 are in close proximity to one another, they form capacitors 168 between the detector 160 and power source and communication device 170.

The inductive coupling between the transmitter coil 177 and receiver coil 167 eliminates a direct connection between the detector 161 and the table, wall stand or mobile X-ray imaging system. The inductive coupling provides a wireless non-contact power path between the power source and communication device 170 and the detector 161 for powering the detector circuitry 162. In an exemplary embodiment, the power source and communication device 170 may be used to power the detector circuitry 162 directly with the selected null frequency power source. Therefore, the charging circuitry 164 and detector battery 163 are not needed and deleted from the embodiment shown in FIG. 10B.

The capacitive coupling between the power source and communication device 170 and detector 161 eliminates a direct connection between the detector 161 and the table, wall stand or mobile X-ray imaging system. The capacitive coupling provides a wireless non-contact communication path between the power source and communication device 170 and the detector 161 for providing communication and data transfer between the power source and communication device 170 and the detector 161.

While the disclosure has been described with reference to various embodiments, those skilled in the art will appreciate that certain substitutions, alterations and omissions may be made to the embodiments without departing from the spirit of the disclosure. Accordingly, the foregoing description is meant to be exemplary only, and should not limit the scope of the disclosure as set forth in the following claims.

What is claimed is:

1. An X-ray imaging system comprising:
    a portable digital X-ray detector including detector circuitry coupled to a detector battery and coupled to at least one receiver coil; and
    a power source including a power supply coupled to an on/off switch and coupled to at least one transmitter coil;
    wherein the power source is coupled to a detector receptacle of the X-ray imaging system; and
    wherein the at least one receiver coil and the at least one transmitter coil are inductively coupled to each other when the portable digital X-ray detector is located within the detector receptacle of the X-ray imaging system to transfer power from the power supply to the detector battery when the on/off switch is in an on position.

2. The X-ray imaging system of claim 1, wherein the detector battery is a rechargeable battery.

3. The X-ray imaging system of claim 2, wherein the portable digital X-ray detector further including charging circuitry coupled between the at least one receiver coil and the detector battery for charging the detector battery from the power inductively coupled from the power supply.

4. The X-ray imaging system of claim 1, wherein the detector battery is used to power the detector circuitry during an imaging mode or a digital cassette mode.

5. The X-ray imaging system of claim 4, wherein the on/off switch is switched to an off position during the imaging mode or the digital cassette mode.

6. The X-ray imaging system of claim 1, wherein the power transfer is a non-contact wireless power transfer.

7. The X-ray imaging system of claim 1, wherein the on/off switch is controlled by the X-ray imaging system.

8. The X-ray imaging system of claim 1, wherein the power supply is decoupled from the at least one transmitter coil when the on/off switch is switched to an off position, eliminating electromagnetic interference (EMI) from the portable digital X-ray detector due to inductive coupling between the at least one transmitter coil and the at least one receiver coil.

9. The X-ray imaging system of claim 1, wherein the portable digital X-ray detector includes EMI shielding.

10. An X-ray imaging system comprising:
a portable digital X-ray detector including detector circuitry coupled to a detector battery and coupled to at least one receiver coil; and
a power source including a power supply coupled to a signal filter device and coupled to at least one transmitter coil;
wherein the power source is coupled to a detector receptacle of the X-ray imaging system; and
wherein the at least one receiver coil and the at least one transmitter coil are inductively coupled to each other when the portable digital X-ray detector is located within the detector receptacle of the X-ray imaging system to transfer power from the power supply to the detector battery.

11. The X-ray imaging system of claim 10, wherein the detector battery is a rechargeable battery.

12. The X-ray imaging system of claim 11, wherein the portable digital X-ray detector further including charging circuitry coupled between the at least one receiver coil and the detector battery for charging the detector battery from the power inductively coupled from the power supply.

13. The X-ray imaging system of claim 10, wherein the detector battery is used to power the detector circuitry during an imaging mode or a digital cassette mode.

14. The X-ray imaging system of claim 10, wherein the power transfer is a non-contact wireless power transfer.

15. The X-ray imaging system of claim 10, wherein the signal filter device is a low-pass filter and wherein the power supply is configured to drive the transmitter coil at a fundamental frequency that is lower than the low-pass filter pass band.

16. The X-ray imaging system of claim 15, wherein the low-pass filter is configured to pass low frequency signals and attenuate high frequency signals from the power supply to the at least one transmitter coil, eliminating high frequency EMI from the portable digital X-ray detector.

17. The X-ray imaging system of claim 10, wherein the signal filter device is a band-pass filter and wherein the power supply is configured to drive the transmitter coil at a fundamental frequency that is within the band-pass filter pass band.

18. The X-ray imaging system of claim 17, wherein the band-pass filter is configured to pass a null frequency signal from the power supply to the at least one transmitter coil, eliminating EMI from the portable digital X-ray detector.

19. The X-ray imaging system of claim 10, wherein the portable digital X-ray detector includes EMI shielding.

20. An X-ray imaging system comprising:
a portable digital X-ray detector including detector circuitry coupled to at least one receiver coil; and
a power source including a power supply coupled to a signal filter device and coupled to at least one transmitter coil;
wherein the power source is coupled to a detector receptacle of the X-ray imaging system; and
wherein the at least one receiver coil and the at least one transmitter coil are inductively coupled to each other when the portable digital X-ray detector is located within the detector receptacle of the X-ray imaging system to transfer power from the power supply to the detector circuitry.

21. The X-ray imaging system of claim 20, wherein the power transfer is a non-contact wireless power transfer.

22. The X-ray imaging system of claim 20, wherein the signal filter device is a low-pass filter and wherein the power supply is configured to drive the transmitter coil at a fundamental frequency that is lower than the low-pass filter pass band.

23. The X-ray imaging system of claim 22, wherein the low-pass filter is configured to pass low frequency signals and attenuate high frequency signals from the power supply to the at least one transmitter coil, eliminating high frequency EMI from the portable digital X-ray detector.

24. The X-ray imaging system of claim 20, wherein the signal filter device is a band-pass filter and wherein the power supply is configured to drive the transmitter coil at a fundamental frequency that is within the band-pass filter pass band.

25. The X-ray imaging system of claim 24, wherein the band-pass filter is configured to pass a null frequency signal from the power supply to the at least one transmitter coil, eliminating EMI from the portable digital X-ray detector.

26. A portable wireless digital X-ray detector comprising:
detector circuitry coupled to a detector battery and charging circuitry;
at least one receiver coil coupled to the charging circuitry;
a wireless antenna coupled to the detector circuitry; and
EMI shielding protecting the detector circuitry, detector battery and charging circuitry from EMI.

27. The portable wireless digital X-ray detector of claim 26, wherein the detector circuitry, detector battery and charging circuitry are electrically shielded from the wireless antenna and the at least one receiver coil by a conductive material or conductive member that provides EMI shielding from the wireless antenna and the at least one receiver coil.

28. A portable wireless digital X-ray detector comprising:
detector circuitry coupled to at least one receiver coil;
a wireless antenna coupled to the detector circuitry; and
EMI shielding protecting the detector circuitry from EMI.

29. The portable wireless digital X-ray detector of claim 28, wherein the detector circuitry is electrically shielded from the wireless antenna and the at least one receiver coil by a conductive material or conductive member that provides EMI shielding from the wireless antenna and the at least one receiver coil.

* * * * *